United States Patent [19]

Ryer et al.

[11] 4,102,798

[45] Jul. 25, 1978

[54] OXAZOLINE ADDITIVES USEFUL IN OLEAGINOUS COMPOSITIONS

[75] Inventors: Jack Ryer, East Brunswick; James Zielinski, Somerset; Harold N. Miller, Millington; Stanley J. Brois, Westfield, all of N.J.

[73] Assignee: Exxon Research & Engineering Co., Linden, N.J.

[21] Appl. No.: 708,925

[22] Filed: Jul. 27, 1976

Related U.S. Application Data

[63] Continuation of Ser. No. 455,250, Mar. 27, 1974, abandoned.

[51] Int. Cl.² .............................................. C10M 1/32
[52] U.S. Cl. .......................... 252/51.5 A; 252/51.5 R; 260/307 F
[58] Field of Search ..................... 252/51.5 R, 51.5 A; 260/307 F

[56]      References Cited
       U.S. PATENT DOCUMENTS

| 2,569,428 | 9/1951 | Rowland ........................... 260/307 F |
|---|---|---|
| 2,831,858 | 4/1958 | de Benneville et al. ..... 260/307 F X |
| 2,905,644 | 9/1959 | Butter .......................... 260/307 F X |
| 3,219,666 | 11/1965 | Norman et al. ............. 252/51.5 A X |
| 3,235,557 | 2/1966 | Wiggins et al. .................. 260/307 F |
| 3,248,397 | 4/1966 | Purcell ............................. 260/307 F |
| 3,966,620 | 6/1976 | Bridger et al. ............. 252/51.5 A X |
| 4,035,309 | 7/1977 | Brois ............................ 252/51.5 A X |
| 4,049,564 | 9/1977 | Ryer et al. ...................... 252/51.5 A |

FOREIGN PATENT DOCUMENTS 1,444,904   2/1969   Fed. Rep. of Germany ... 252/51.5 A Primary Examiner—Delbert E. Gantz
Assistant Examiner—Andrew H. Metz
Attorney, Agent, or Firm—Frank T. Johmann; Roland A. Dexter

[57]      ABSTRACT

Oil soluble oxazoline reaction products of hydrocarbon substituted dicarboxylic acid, ester, or anhydride, for example polyisobutenylsuccinic anhydride, with 2,2-disubstituted-2-amino-1-alkanols, such as tris-hydroxymethylaminomethane (THAM), are useful additives in oleaginous compositions, such as sludge dispersants for lubricating oil or gasoline.

31 Claims, No Drawings

OXAZOLINE ADDITIVES USEFUL IN OLEAGINOUS COMPOSITIONS

This is a continuation, of application Ser. No. 455,250, filed Mar. 27, 1974 now abandoned.

BACKGROUND OF THE INVENTION AND PRIOR ART

During the past decade, ashless sludge dispersants have become increasingly important, primarily in improving the performance of lubricants and gasoline in keeping the engine clean of deposits and permitting extended crankcase oil drawn periods. Most commercial ashless dispersants fall into several general categories. In one category, an amine or polyamine is attached to a long chain hydrocarbon polymer, usually polyisobutylene, directly by reaction of halogenated olefin polymer with polyamine as in U.S. Pat. Nos. 3,275,554; 3,565,592; 3,565,804. In another category, a polyamine is linked to the polyisobutylene through an acid group, such as long chain monocarboxylic acid, e.g., see U.S. Pat. No. 3,444,170 or long chain dicarboxylic acid such as polyisobutenylsuccinic anhydride, by forming amide or imide linkages, such as described in U.S. Pat. Nos. 3,172,892; 3,219,666; etc. More recently, non-nitrogen ashless dispersants have been formed by esterifying long chain dicarboxylic acids; such as the polyisobutenylsuccinic anhydride, with polyols, such as pentaerythritol, as in U.S. Pat. No. 3,381,022.

Reaction products of hydrocarbon substituted succinic anhydride, e.g., the aforesaid polyisobutenylsuccinic anhydride, with compounds containing both an amine group and a hydroxy group have been suggested or investigated in the prior art. For example, U.S. Pat. No. 3,272,746 teaches the reaction of ethanolamine and diethanolamine, as well as various hydroxyalkyl substituted alkylene amines, such as N-(2-hydroxyethyl) ethylene diamine, N,N'-bis(2-hydroxyethyl) ethylene diamine, with alkenyl succinic anhydride to obtain ashless dispersants for lube oil. A hydroxy amine, such as diethanolamine, is reacted with a long chain alkenylsuccinic anhydride in U.S. Pat. No. 3,324,033 to form a mixture of esters and amides, wherein some of the diethanolamine reacts through a hydroxy group to give an ester linkage, which another portion of the diethanolamine forms an amide linkages. U.S. Pat. No. 3,364,001 teaches a tertiary alkanolamine reacted with an alkenyl succinic anhydride to form an ester useful as a gasoline additive. U.S. Pat. No. 3,448,049 teaches dispersants, corrosion inhibitors and antiwear agents in lubricants and fuels by esterifying alkenyl succinic anhydride with a hydroxy compound made by reacting an alkanolamine with an unsaturated ester, amide or nitrile. U.S. Pat. No. 3,630,904 teaches reacting a hydroxy amine with both short and long chain dicarboxylic acid. U.S. Pat. No. 3,484,374 teaches the polymeric condensation product of polycarboxylic acid or anhydride with various alkanolamines such as aminoethyl ethanolamine, N-methyldiethanolamine, etc.

U.S. Pat. No. 3,576,743 teaches reacting polyisobutenylsuccinic anhydride with a polyol, such as pentaerythritol, followed by reaction with trismethylolaminomethane (THAM), (see Example 1). U.S. Pat. No. 3,632,511 teaches reacting polyisobutenylsuccinic anhydride with both a polyamine and a polyhydric alcohol including THAM. U.S. Pat. No. 3,697,428 (Example 11) teaches reacting polyisobutenylsuccinic anhydride with a mixture of pentaerythritol and THAM.

SUMMARY OF THE INVENTION

As noted above, the prior art teaches dispersants formed from long chain hydrocarbyl substituted dicarboxylic acid material, usually alkenyl succinic anhydride, reacted with various amino or hydroxy compounds, either through an amide, imide, or ester linkage. In contrast to the prior art, the present invention is based upon the discovery that reaction of long chain hydrocarbyl dicarboxylic acid material, i.e., acid, or anhydride, or ester, with certain classes of amino alcohols, under certain conditions, will result in a different type of linkage, namely an oxazoline linkage, and that materials with this oxazoline linkage appear very effective as detergents or dispersants for oleaginous compositions such as lube oil and gasoline.

THE HYDROCARBYL DICARBOXYLIC ACID MATERIAL

The long chain hydrocarbyl substituted dicarboxylic acid material, i.e., acid or anhydrie, or ester, used in the invention includes alpha-beta unsaturated $C_4$ to $C_{10}$ dicarboxylic acids, or anhydrides or esters thereof, such as fumaric acid, itaconic acid, maleic acid, maleic anhydride, chloromaleic acid, dimethyl fumarate, etc. which are substituted with a long hydrocarbon chain, generally a olefin polymer chain.

In general, these hydrocarbyl substituted dicarboxylic acid materials and their preparation are well known in the art, for example see U.S. Pat. Nos. 3,219,666; 3,172,892; 3,272,746; as well as the aforementioned prior art patents.

The hydrocarbyl portion should average at least 50 aliphatic carbon atoms per dicarboxylic acid group and be substantially saturated. Usually no more than 10 mole %, and preferably 5 mole % or less, of the total carbon to carbon linkage will be unsaturated, as excessive unsaturation in the final product will tend to oxidize and unduly form gums and resins in the engine. Further descriptions and examples of the hydrocarbyl substituent portion are set forth in U.S. Pat. No. 3,272,746, column 2, line 35 to column 4, line 10, which is hereby incorporated in this application by reference.

Frequently these hydrocarbyl substituted dicarboxylic acid materials are prepared by reacting the unsaturated dicarboxylic acid material, usually maleic anhydride, with an olefin, usually an olefin polymer still retaining a terminal unsaturation. The olefin polymer can, if desired, be first halogenated, for example, chlorinated or brominated to about 2 to 5 wt. % chlorine, or about 4 to 8 wt. % bromine, based on the weight of polymer, and then reacted with the maleic anhydride (see U.S. Pat. No. 3,444,170).

In some cases, the olefin polymer may be completely saturated, for example an ethylene-propylene copolymer made by a Ziegler-Natta synthesis using hydrogen as a moderator to control molecular weight. In the case of such saturated polymers, then the polymer can be halogenated to make it reactive so it can be condensed with the unsaturated dicarboxylic acid material which is then randomly added along the polymer chain.

Preferred olefin polymers for reaction with the unsaturated dicarboxylic acids are polymers comprising a major molar amount of $C_2$ to $C_5$ monoolefin, e.g., ethylene, propylene, butylene, isobutylene and pentene. The polymers can be homopolymers such as polyisobutylene, as well as copolymers of two or more of such olefins such as copolymers of: ethylene and propylene; butylene and isobutylene; propylene and isobutylene; etc. Other compolymers include those in which a minor molar amount of the copolymer monomers, e.g., 1 to 20 mole %, is a $C_4$ to $C_{18}$ non-conjugated diolefin, e.g., a copolymer of isobutylene and butadiene; or a copolymer of ethylene, propylene and 1,4-hexadiene; etc.

The olefin polymers will usually have number average molecular weights within the range of about 750 and about 200,000, more usually between about 1000 and about 20,000. Particularly useful olefin polymers have number average molecular weights within the range of about 900 and about 3000 with approximately one terminal double bond per polymer chain. An especially valuable starting material for a highly potent dispersant additive made in accordance with this invention is polyisobutylene.

Especially useful when it is desired that the dispersant additives also possess viscosity index improving properties are 10,000 to 200,000, e.g., 25,000 to 100,000 number average molecular weight polymers. An especially preferred example of such a V.I. improving polymer is a copolymer of about 30 to 85 mole % ethylene, about 15 to 70 mole % $C_3$ to $C_5$ mono-alphaolefin, preferably propylene, and 0 to 20 mole % of a $C_4$ to $C_{14}$ non-conjugated diene.

These ethylene-propylene V.I. improving copolymers or terpolymers are usually prepared by Ziegler-Natta synthesis methods, e.g., see U.S. Pat. No. 3,551,336. Some of these copolymers and terpolymers are commercially available, such as VISTALON ®, an elastomeric terpolymer of ethylene, propylene and 5-ethylidene norbornene, marketed by Exxon Chemical Co., New York, N.Y. and NORDEL ®, a terpolymer of ethylene, propylene and 1,4-hexadiene marketed by E.I. duPont DeNemours & Co.

Other halogenation techniques for attaching the dicarboxylic acid material to a long hydrocarbon chain, involve first halogenating the unsaturated dicarboxylic acid material and then reacting with the olefin polymer, or by blowing halogen gas, e.g., chlorine, through a mixture of the polyolefin and unsaturated dicarboxylic acid material, then heating to 150° to 220° C. in order to remove HCl gas, e.g., see U.S. Pat. Nos. 3,381,022 and 3,565,804.

THE AMINO ALCOHOL

The amino alcohol used to make the oxazoline dispersant is a 2,2-disubstituted-2-amino-1-alkanol, having 2 to 3 hydroxy groups, containing a total of 4 to 8 carbon atoms, and which can be represented by the formula:

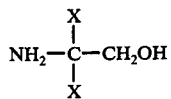

wherein X is an alkyl, or hydroxy alkyl group, with at least one of the X substituents, and preferably both of the X substituents, being a hydroxy alkyl group of the structure $-(CH_2)_nOH$, wherein $n$ is 1 to 3.

Examples of such 2,2-disubstituted amino alkanols, include 2-amino-2methyl-1,3-propanediol, 2-amino-2-(hydroxymethyl)-1,3-propanediol (also known as tris-hydroxyaminomethane or THAM), 2-amino-2-ethyl-1,3-propanediol, etc. Because of its effectiveness, availability, and cost, the THAM is particularly preferred.

THE OXAZOLINE REACTION CONDITIONS

The formation of the novel oxazoline dispersants, in a fairly higher yield, can be effected by adding about 1 to 2 mole equivalent of the aforesaid 2,2-disubstituted-2-amino-1-alkanol per mole equivalent of the dicarboxylic acid material, with or without an inert diluent, and heating the mixture at 140°–240° C., preferably 180°–220° C. for ½ to 24, more usually 2 to 8 hours.

Although not necessary, the presence of small amounts, such as 0.01 to 2 wt. %, preferably 0.1 to 1 wt. %, based on the weight of the reactants, of a metal salt can be used in the reaction mixture as catalyst to shorten the reaction times. The metal catalyst can later be removed by filtration or by washing a hydrocarbon solution of the product with a lower alcohol, such as methanol, ethanol, isopropanol, etc., or an alcohol/water solution.

Alternatively, the metal salt can be left in the reaction mixture, as it appears to become stably dispersed, or dissolved, in the reaction product, and, depending on the metal, it may even contribute performance benefits to the oil or gasoline. This is believed to occur with the use of zinc catalysts.

Inert solvents which may be used in the above reaction include hydrocarbon oils, e.g., mineral lubricating oil, kerosene, neutral mineral oils, xylene, halogenated hydrocarbons, e.g., carbon tetrachloride, dichlorobenzene, tetrahydrofuran, etc.

Metal salts that may be used as catalysts in the invention include carboxylic acid salts of Zn, Co, Mn and Fe. Metal catalysts derived from strong acids (HCl, sulfonic acid, $H_2SO_4$, $HNO_3$, etc.) and bases tend to diminish the yield of the oxazoline products and instead favor imide or ester formation. For this reason, these strong acid catalysts or basic catalysts are not preferred and usually will be avoided. The carboxylic acids used to prepare the desired catalysts, include $C_1$ to $C_{18}$, e.g., $C_1$ to $C_8$, acids, such as the saturated or unsaturated mono and dicarboxylic aliphatic hydrocarbon acis, particularly fatty acids. Specific examples of such desired carboxylic acid salts include zinc acetate, zinc formate, zinc propionate, zinc stearate, manganese (ous) acetate, iron tartrate, cobalt (ous) acetate, etc. Completion of the oxazoline reaction can be readily ascertained by using periodic infrared spectral analysis for following the oxazoline formation (oxazoline peak forms at 6.0 microns), or by the cessation of water evolution.

REACTION MECHANISM OF THE OXAZOLINE FORMATION

While not known with complete certainty, but based on experimental evidence, it is believed that the reaction of the hydrocarbyl substituted dicarboxylic acid material, e.g., a hydrocarbyl substituted succinic anhydride, with the amino alcohol of the invention, e.g., two equivalents of 2,2-disubstituted-2-aminoethanol such as tris-(hydroxymethyl) aminomethane (THAM), gives oxazoline, e.g., bis-oxazolines, via the intermediary of several discrete reaction species. If an acid anhydride is used, the initial transformation appears to involve the scission of the anhydride by the amino function of one mole of the amino alcohol to yield an amic acid. Addition of another mole equivalent of amino alcohol is believed to form the amic acid amine salt, which then upon further heating, undergoes cyclo-dehydration to the final bis-oxazoline product. The catalyst effect of metal salts, such as zinc acetate ($ZnAc_2$), on oxazoline formation is very likely ascribable to the favorable polarization of the amide group by the zinc ion towards attack by the hydroxy function of the amino alcohol reactant. These reactions can be typified as follows in the case of bis-oxazoline:

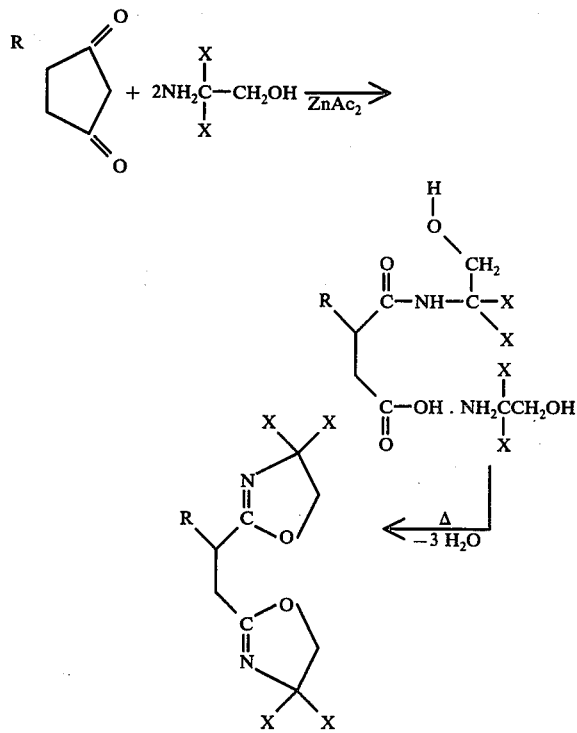

where R is the hydrocarbyl group of the succinic anhydride, and each X in this case of using tris-(hydroxymethyl) amino methane (THAM) represents a —CH$_2$OH group.

In contrast to the above oxazoline formation using the disubstituted amino alcohol, if the amino alcohol has no substituents as in 2-aminoethanol, or has only one substituent in the 1- or 2-position as in 2-amino-1-propanol, 2-amino-1-butanol, and related mono-substituted 2-aminoethanols, the amino alcohol fails to undergo the aforesaid oxazoline reaction. Instead, these other amino alcohols will react with the succinic anhydride to give almost exclusively succinimide products as illustrated in the following reaction.

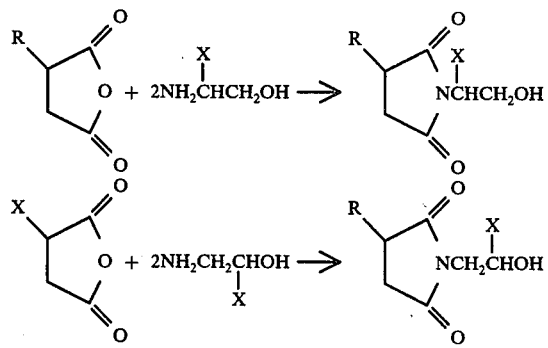

wherein R and X are as previously defined. In experiments on the above reactions, in no instance were discernible amounts of bis-oxazoline products found.

USE OF THE OXAZOLINE ADDITIVE IN OLEAGINOUS COMPOSITIONS

The oil soluble oxazoline reaction products of this invention can be incorporated in a wide variety of oleaginous compositions. They can be used in lubricating oil compositions, such as automotive crankcase lubricating oils, automatic transmission fluids, etc. in concentrations generally within the range of about 0.01 to 20 weight percent, e.g., 0.1 to 10 weight percent, preferably 0.3 to 3.0 weight percent, of the total composition. The lubricants to which the oxazoline products can be added include not only hydrocarbon oils derived from petroleum, but also include synthetic lubricating oils such as polyethylene oils; alkyl esters of dicarboxylic acid; complex esters of dicarboxylic acid, polyglycol and alcohol; alkyl esters of carbonic or phosphoric acids; polysilicones; fluorohydrocarbon oils; mixtures of mineral lubricating oil and synthetic oils in any proportion, etc.

When the products of this invention are used as detergents or dispersants in fuels such as gasoline, kerosene, diesel fuels, No. 2 fuel oil and other middle distillates, a concentration of the additive in the fuel in the range of 0.001 to 0.5 weight percent, based on the weight of the total composition, will usually be employed.

When used as an antifoulant in oil streams in refinery operations to prevent fouling of process equipment such as heat exchangers, about 0.001 to 2 wt. % will generally be used.

The additive may be conveniently dispensed as a concentrate comprising a minor proportion of the additive, e.g., 2 to 45 parts by weight, dissolved in a major proportion of a mineral lubricating oil, e.g., 98 to 45 parts by weight, with or without other additives being present.

In the above compositions of concentrates, other conventional additives may also be present, including dyes, pour point depressants, antiwear agents such as tricresyl phosphate or zinc dialkyl dithiophosphates of 3 to 8 carbon atoms in each alkyl group, antioxidants, such as N-phenyl α-naphthylamine, tert-octyl phenol sulfide, 4,4'-methylene bis(2,6-di tert-butyl phenol), viscosity index improvers such as ethylene-propylene copolymers, polymethacrylates, polyisobutylene, alkyl fumarate-vinyl acetate copolymers and the like, as well as other ashless dispersants, detergents and viscosity index improvers, etc.

This invention will be further understood by reference to the following examples, which include preferred embodiments of the invention.

EXAMPLE 1

A bis oxazoline of polyisobutenylsuccinic anhydride and tris-(hydroxymethyl) aminomethane was prepared as follows:

280 gms. (0.5 equivalent) of polyisobutenylsuccinic anhydride was charged into a laboratory glass 1 liter reaction flask, equipped with a bottom draw-off, a thermometer, a charging funnel, a nitrogen bleed, and an overhead condensor equipped with a Deane-Starke water trap. The flask was heated in an oil bath. The anhydride was then heated to about 200° C. under a blanket of nitrogen. While stirring at this temperature, 0.5 mole (60.5 g.) of tris-(hydroxymethyl) aminomethane (THAM) was added in a series of portions of about 5 grams each, over an hour period with stirring. Thereafter, the reaction was continued with stirring at 200° C.

for 2 hours while collecting water from the condenser. The flask was then allowed to cool and a liter of hexane was added to the flask to dissolve the reaction product, which was then drained from the flask and filtered through filter paper to remove any solids. The hexane solution was then washed three times with 250 ml. portions of methanol. Thereafter the hexane layer was placed in a rotoevaporator at 90° C. for about 2 hours to evaporate off the hexane. Then an equal weight of a neutral mineral lubricating oil having a viscosity of about 150 SUS at 100° F. (Solvent 150 Neutral) was added with stirring to give an oil concentrate consisting of about 50 wt. % of the oxazoline reaction product in about 50 wt. % mineral lubricating oil. The infrared spectrum of this concentrate product featured a strong absorption band at about 6.0 microns as expected for the bis-oxazoline. The product (50% active ingredient in Solvent 150 Neutral Oil) analyzed for 0.78 wt. % nitrogen and 2.30 wt. % oxygen. The observed oxygen to nitrogen (O/N) ratio of 2.95 is in excellent agreement with the theoretical O/N ratio of 3. The product showed a total acid number (ASTM-D664) of 0.03.

The polyisobutenylsuccinic anhydride used above had been prepared by conventional techniques, namely the reaction of chlorinated polyisobutylene having a chlorine content of about 3.8 wt. %, based on the weight of chlorinated polyisobutylene, and an average of 70 carbon atoms in the polyisobutylene group, with maleic anhydride at about 200° C. The resulting polyisobutenyl succinic anhydride showed a saponification number (Sap. No.) of 80 mg KOH/gm.

EXAMPLE 2

A mixture of 500 gm. (0.78 equivalent) of polyisobutenylsuccinic anhydride having a Sap No. of 87, 500 ml. of tetrahydrofuran (THF) as solvent, 4 gm. of zinc acetate dihydrate (ZnAc$_2$.2H$_2$O) as a catalyst and 96.8 gm. (0.8 mole) of tris-(hydroxymethyl) aminomethane (THAM) was charged into the previously described glass reactor and heated. When the reaction temperature had risen to 72° C., the THF solvent distilled off. Further heating at about 200° C. for four hours gave the expected quantity of water, i.e., about 1.1 moles of water in the trap. After filtration, the reaction product analyzed for 1.99 wt. % nitrogen, and 0.12 wt. % zinc. The product was drawn from the flask and diluted with an equal weight of the Solvent 150 Neutral mineral lubricating oil for testing in the Sludge Inhibition Bench (SIB) test to be later described.

The polyisobutenyl group of the succinic anhydride averaged about 70 carbon atoms.

EXAMPLE 3

A mixture of 500 gm. (0.78 equivalent) of the polyisobutenylsuccinic anhydride of Example 2, 96.8 gm. (0.8 moles) of tris-(hydroxymethyl) aminomethane and 4.0 gms. of zinc acetate dihydrate were charged into the glass reactor previously described. The mixture was heated in the oil bath at about 200°–220° C. for about three hours, until water ceased to evolve from the reactor. Approximately 18.0 gm. (1 mole) of water collected in the trap. The infrared spectrum of the reaction product drawn from the flask showed a strong absorption band at 6.0 microns showing the oxazoline structure had formed. Elemental analysis showed that the final product of 50 wt. % of the reaction product dissolved in 50 wt. % Solvent 150 Neutral oil, contained 1.08% nitrogen and 0.058% zinc.

EXAMPLE 4

A mixture of 60.57 pounds (44.0 moles) of polyisobutenylsuccinic anhydride of Example 2, 11.73 pounds (27.5 moles) of THAM, and 0.48 pounds (1 mole) of zinc acetate dihydrate as catalyst, were charged into a small pilot plant stirred reactor equipped with a nitrogen purge, stirrer, and overhead condensor with a water trap. The reaction mixture was heated to 427° F. at a rate of 122° F. per hour and held on temperature until 3.35 pounds (ca. 84.49 moles) of water of reaction was produced. Thereafter, the reaction contents were cooled and diluted with the aforesaid Solvent 150 Neutral oil to give a 50 wt. % solution of the reaction product in 50 wt. % oil. This oil concentrate showed a Hydroxyl Number of 37.0 and contained 0.92 wt. % nitrogen and 0.05 wt. % zinc, based on the weight of the concentrate.

EXAMPLES 5 to 23

Using the same general procedure as described in Example 3, various polyisobutenylsuccinic anhydrides (PIBSA) of polyisobutylene having number average molecular weights of 980, 2300 and 18,000 were reacted with 2 mole equivalents of various amino alcohols to form bis-oxazolines, including 2-amino-2-methyl-1-propanol (AMP), 2-amino-2-methyl-1,3-propane-diol (AMPD) and 2-amino-2-(hydroxymethyl)-1,3-propanediol (THAM).

The reactants, proportions, and analyses of the products formed in Examples 1 to 23 are summarized in Table I.

TABLE I

OXAZOLINE ADDUCTS OF POLYISOBUTENYLSUCCINIC ANHYDRIDE AND 2,2-DISUBSTITUTED-2-AMINO ETHANOLS

| Example | PIBSA PIB Mw[a] | PIBSA Sap. No. | PIBSA Grams Used | Amino Alcohol Type[b] | Amino Alcohol Grams Used | Zinc Salt[c] Grams Used | Analyses of Concentrate[d] % Wt. N | Analyses of Concentrate[d] % Wt. Zn | Analyses of Concentrate[d] % Wt. O$_2$ |
|---|---|---|---|---|---|---|---|---|---|
| 1 | 980 | 80 | 280 | THAM | 60.5 | 0 | .78 | 0 | 2.30 |
| 2 | 980 | 87 | 500 | THAM | 96.8 | 4.0 | 1.99 | 0.12 | — |
| 3 | 980 | 87 | 500 | THAM | 96.8 | 4.0 | 1.08 | 0.058 | — |
| 4 | 980 | 84 | 27,500 | THAM | 5,300 | 220 | .92 | .05 | — |
| 5 | 980 | 80 | 500 | AMP | 71.2 | 4 | 0.89 | 0.07 | — |
| 6 | 980 | 112 | 500 | AMP | 100.0 | 4 | 1.16 | .01 | — |
| 7 | 980 | 112 | 150 | AMP | 26.8 | 0 | .90 | — | 1.10 |
| 8 | 980 | 112 | 150 | AMP | 28 | 0 | .95 | — | 1.60 |
| 9 | 980 | 80 | 350 | AMPD | 79 | 1.4 | — | — | — |
| 10 | 980 | 80 | 500 | THAM | 96.8 | 4.0 | .99 | 0.12 | — |
| 11 | 980 | 80 | 350 | THAM | 60.5 | 2.7 | 0.93 | .017 | — |
| 12 | 980 | 80 | 350 | THAM | 60.5 | 0 | 1.15 | — | — |
| 13 | 980 | 112 | 150 | THAM[e] | 36.3 | 0 | 1.18 | — | — |

TABLE I-continued
OXAZOLINE ADDUCTS OF POLYISOBUTENYLSUCCINIC ANHYDRIDE AND 2,2-DISUBSTITUTED-2-AMINO ETHANOLS

| | PIBSA | | | Amino Alcohol | | Zinc Salt[c] | Analyses of Concentrate[d] | | |
|---|---|---|---|---|---|---|---|---|---|
| Example | PIB Mw[a] | Sap. No. | Grams Used | Type[b] | Grams Used | Grams Used | % Wt. N | % Wt. Zn | % Wt. O$_2$ |
| 14 | 980 | 112 | 500 | THAM[e] | 121 | 0 | 1.2 | — | 3.58 |
| 15 | 980 | 112 | 2000 | THAM[e] | 484 | 0 | 1.38 | — | 3.31 |
| 16 | 980 | 112 | 600 | THAM[e] | 145.2 | 4 | 1.17 | — | 3.57 |
| 17 | 980 | 112 | 500 | THAM[e] | 121 | 4 | 1.19 | .01 | — |
| 18 | 980 | 112 | 500 | THAM | 121 | 4 | 1.28 | .06 | — |
| 19 | 980 | 112 | 520 | THAM | 121 | 0 | 1.43 | — | — |
| 20 | 980 | 80 | 350 | THAM AMP | .8 24.51 | 1.31 | 1.18 | — | — |
| 21 | 18,000 | 1.9 | 200[f] | THAM | .86 | 0.07 | — | — | — |
| 22 | 18,000 | 1.9 | 200[f] | THAM | .73 | 0.08 | — | — | — |
| 23 | 18,000 | 1.9 | 2000[f] | THAM | 7.3 | 0.8 | — | — | — |

[a]Molecular weight of the polyisobutenyl group (PIB) by Vapor Pressure Osmometry (VPO)

[b]AMP = 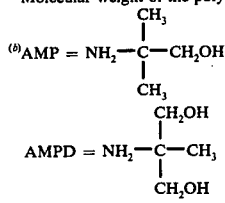

AMPD = 

THAM = $NH_2C(CH_2OH)_3$

[c]Zinc diacetate dihydrate.
[d]Analyses on 50 wt. % solution of the oxazoline reaction product in 50 wt. % Solvent 150 Neutral mineral lubricating oil.
[e]THF used to dissolve THAM.
[f]20 wt. % solution in S 150 N.
[g]30.3 gm. of THAM added over 1 hour, then 24.51 of AMP added over 1 hour.

SLUDGE INHIBITION BENCH (SIB) TEST

A number of the additives of this invention were subjected to a Sludge Inhibition Bench (SIB) Test which has been found, after a large number of evaluations, to be an excellent test for assessing the dispersing power of lubricating oil dispersant additives.

The medium chosen for the Sludge Inhibition Bench Test was a used crankcase mineral lubricating oil composition having an original viscosity of about 325 SUS at 100° F. that had been used in a taxicab that was driven generally for short trips only, thereby causing a buildup of a high concentration of sludge precursors. The oil that was used contained only a refined base mineral lubricating oil, a viscosity index improver, a pour point depressant and zinc dialkyldithiophosphate antiwear additive. The oil contained no sludge dispersants. A quantity of such used oil was acquired by draining and refilling the taxicab crankcase at 1000-2000 mile intervals.

The Sludge Inhibition Bench Test is conducted in the following manner. The aforesaid used crankcase oil, which is milky brown in color, is freed of sludge by centrifuging for 1 hour at about 39,000 gravities (gs.). The resulting clear bright red supernatant oil is then decanted from the insoluble sludge particles thereby separated out. However, the supernatant oil still contains oil-soluble sludge precursors which on heating under the conditions employed by this test will tend to form additional oil-in-soluble deposits of sludge. The sludge inhibiting properties of the additives being tested are determined by adding to portions of the supernatant used oil, a small amount, such as 0.3, 0.5, 1 or 2 weight percent, on an active ingredient basis, of the particular additive being tested. Ten grams of each blend being tested is placed in a stainless steel centrifuge tube and is heated at 280° F. for 16 hours in the presence of air. Following the heating, the tube containing the oil being tested is cooled and then centrifuged for 30 minutes at about 39,000 gs. Any deposits of new sludge that form in this step are separated from the oil by decanting the supernatant oil and then carefully washing the sludge deposits with 25 ml. of pentane to remove all remaining oil from the sludge. Then the weight of the new solid sludge that has been formed in the test, in milligrams, is determined by drying the residue and weighing it. The results are reported as milligrams of sludge per 10 grams of oil, thus measuring differences as small as 1 part per 10,000. The less new sludge formed the more effective is the additive as a sludge dispersant. In other words, if the additive is effective, it will hold at least a portion of the new sludge that forms on heating and oxidation, stably suspended in the oil so it does not precipitate down during the centrifuging.

Using the above described test, the dispersant action of oxazoline additives of the present invention was compared with the dispersing power of a commercial dispersant referred to as PIBSA/TEPA. The PIBSA/-TEPA was prepared by reaction of 1 mole of tetraethylene pentamine with 2.8 moles of polyisobutenylsuccinic anhydride obtained from polyisobutylene of about 1000 number average molecular weight. The PIBSA/TEPA dispersant was used in the form of an additive concentrate containing about 50 weight percent PIBSA/-TEPA in 50 wt. % mineral lubricating oil. This PIB-SA/TEPA additive concentrate analyzed about 1.14% nitrogen, indicating that the active ingredient, i.e., PIB-SA/TEPA per se, contained about 2.28% nitrogen. Sufficient quantities of all the additive concentrates tested below were used in making the test blends to furnish the 1.0, 0.5, and 0.3 weight percent of actual additive. The test results are given in Table II.

TABLE II
SLUDGE DISPERSANCY TEST RESULTS

| Additive of | Mg. Sludge/10 g. Oil at | | |
|---|---|---|---|
| Example | 1.0 Wt. % | 0.5 Wt. % | 0.3 Wt. % |
| 10 | 1.6 | 6.6 | — |
| 15 | 3.5 | — | — |

TABLE II-continued

SLUDGE DISPERSANCY TEST RESULTS

| Additive of Example | Mg. Sludge/10 g. Oil at | | |
|---|---|---|---|
| | 1.0 Wt. % | 0.5 Wt. % | 0.3 Wt. % |
| 14 | 3.8 | — | — |
| 12 | 2.9 | 5.9 | 7.3 |
| 11 | 2.7 | 6.1 | 7.3 |
| 21 | 2.6 | 5.9 | — |
| 22 | 2.8 | 6.3 | — |
| 23 | 2.0 | 4.1 | — |
| PIBSA-TEPA | 5.2 | 7.5 | 7.7 |

It will be noted from Table II that the dispersants of the invention were more effective than the commercial PIBSA/TEPA dispersant which is in widespread use in crankcase lubricating formulations. Specifically 1.0 wt. % of PIBSA/TEPA per se (i.e., 2 wt. % of its 50 wt. % concentrate) gave 5.2 mg. of new sludge precipitated, per 10 gms. of crankcase oil. On the other hand, the bis-oxazoline products of the invention shown in Table II, were more effective as sludge dispersants since they stably suspended a larger proportion of the new sludge as shown by the fact that less sludge precipitated down during the centrifugation. Similar results are shown at the 0.5 wt. %, and 0.3 wt. % active ingredient levels.

ENGINE TESTS

Lubricant A — This was a SAE Grade 30 crankcase lubricant formulation for automotive crankcase application that was used as a reference. The reference formulation contained mineral lubricating oil, 4.68 wt. % of the aforesaid PIBSA-TEPA ashless dispersant concentrate, and a series of conventional additives, namely, a $P_2S_5$ treated alpha pinene as an oxidation, corrsion inhibitor; and as detergent inhibitor additives, a zinc dialkyl dithiophosphate, barium sulfonate, and an overbased barium detergent comprising barium carbonate formed in the presence of $P_2S_5$ treated polyisobutylene and alkyl phenol as surfactants; along with an anti-rust additive.

Lubricants B to E — These lubricants were indentical with Lubricant A described above, except that the 4.68 wt. % of the 50 wt. % concentrate of the PIBSA-TEPA ashless dispersant was omitted, and the inventive oxazoline dispersant of Example 4 was used in varying amounts as follows: Lubricant B — 4.68 wt. %; Lubricant C — 3.76 wt. %; Lubricant D — 3.25 wt. % and Lubricant E — 2.75 wt. % of the 50 wt. % concentrate of oxazoline of Example 4.

Lubricants A to E described above were tested in a MS Sequence VC Engine Test, which is well known in the automotive industry, being described in the publication entitled "Multicylinder Test Sequences for Evaluating Automotive Engine Oils" which is ASTM Special Publication 315-E. At the end of each test, various parts of the engine are rated on a merit basis of 0 to 10, wherein 10 represents a perfectly clean part while the lesser numbers represent increasing degrees of deposit formation. The various ratings are then totaled and averaged on a basis of 10 as a perfect rating. The results obtained with the compositions described above are given in Table III.

TABLE III

MS SEQUENCE VC TEST RESULTS
Merit Ratings (Basis 0 to 10)

| | Lubricant | | | | |
|---|---|---|---|---|---|
| | A | B | C | D | E |
| Sludge Merit | 9.2/9.2 | 9.5 | 9.2 | 9.0 | 8.5 |
| Varnish Merit | 8.2/7.7 | 8.8 | 8.2 | 8.4 | 8.0 |
| Piston Skirt Varnish Merit | 8.4/7.9 | 8.8 | 8.7 | 8.4 | 8.6 |
| PIBSA-TEPA (50% a.i., i.e., active ingredient) | 4.68% | — | — | — | — |
| Example 4 (50% a.i., i.e., active ingredient) | — | 4.68% | 3.76% | 3.25% | 2.75% |

As seen by Table III, two engine runs were made on the PIBSA-TEPA containing formulation. However, taking the better of the two runs on Lubricant A, it is seen that the bix-oxazoline dispersant of Example 4 was superior at the 4.68 and the 3.76 wt. % concentrations, indicating the higher effectiveness of the oxazoline. Considering varnish, the oxazoline was as effective as the PIBSA-TEPA even at the 3.25 wt. % level, and almost as effective at the 2.75 wt. % level (i.e., 1.38 wt. % actual ingredient). Thus, in an important industry test, the oxazoline dispersants were very effective. These engine test results shown that the oxazoline additive c this invention, was not only a good sludge dispersant as shown by Sludge Merit, but also possesses good oxidation control as shown by the reduction in varnish deposits (Varnish Merit) on the various engine parts, and particularly on the piston skirts (Piston Skirt Varnish Merit). This favorable antioxidant property of the oxazoline dispersant additive diminishes the need for additional conventional antioxidants.

Lubricants A and B were tested in the Caterpillar 1-H test (MIL-L-2104B). Following in Table IV are the results of two such engine tests on each Lubricant, showing the piston cleanliness.

TABLE IV

CATERPILLAR 1-H TEST - 480 HOURS

| | Lubricant | | |
|---|---|---|---|
| | A | B | Requirements[1] |
| TGF(%) | 13/28 | 18/4 | 30 max. |
| 2nd groove | 24/3 | 0/10 | 30 max. |
| 1st Land | 16/16 | 7/3 | 60 max. |
| Below | 0/0 | 6/0 | 0 |
| Rating | Pass/Pass | BLPass/Pass | |

[1]Requirements are estimates, actually certification of a piston is done by inspection and some variations from the limit shown are allowed based on the total condition of the piston.

As seen by Table IV, Lubricant B containing the oxazoline dispersant gave exceptionally low deposits as indicated by the % top groove fill (TFG), the amount of deposit in the second ring groove, and the deposits on the first land area, although one of the two runs was a borderline pass (B/L pass) due to deposits below the second groove (Below). This, however, can be overcome by changes in the formulation.

EXAMPLE 24

Part A — 350 gms. (0.328 moles) of polyisobutenyl-succinic anhydride having an ASTM saponification number of about 105 and a molecular weight of about 1067 was reacted with 79.4 gms. (0.656 moles) of 2-amino-2-(hydroxymethyl) 1,3-propanediol (THAM) as follows: the polyisobutenylsuccinic anhydride and THAM were dissolved in 250 ml xylene in a 2 liter 4-neck flask equipped with thermometer, stirrer, dropping funnel, a condenser including a Deane-Starke water trap, and having a nitrogen bleed to provide a nitrogen blanket. The heat was raised to about 290° to 306° F. and over a period of one hour and 45 minutes, about 9 cc water collected in the trap. The heat was then turned off overnight and the following day the reaction mixture was refluxed another hour at 308° F. wherupon 10 cc of water had now collected in the trap. The reaction mixture was then sparged with nitrogen to evaporate the xylene during which time the temperature rose to 380° F. Then the system was connected to a vacuum pump and heated to about 360°–380° F. for 3 hours under a pressure of about 20–30 mm. Hg. The heat was then turned off overnight. The following day the mixture, which was not free of xylene, was warmed to 200° F. and 489 cc (419 gm.) xylene was added to make a concentrate containing 50 wt. % of the bis-oxazoline reaction product dissolved in the xylene to give a concentrate having a nitrogen content of 1.23 wt. % against calculated nitrogen content of 1.1 wt. %.

Part B — A sample of the concentrate product of Part A above was added to a gasoline in an amount equivalent to 25 lbs. of the concentrate (50% a.i.) per 1000 barrels of gasoline. This additive treated gasoline was then tested for its effectiveness in a carburetor detergent test described as follows:

The test gasoline was a MS-08 gasoline which contained about 0.8 wt. % sulfur and which accelerated the formation of carburetor deposits. The tests was carried out by operating a specially fitted 280 cubic inch displacement V-8 test engine fitted with two separate carbutetors leading to opposite manifolds on either side of the engine. Blowby from the engine was cycled back to the intake of the carburetors. In each carburetor was a metal sleeve which could be readily removed and weighed to determine the amount of deposits that has accumulated on the sleeve. The engine was operated for 24 hours under no load through a test cycle of 8 minutes idle at 700 rpm, and then 30 seconds at 2500 rpm, followed by repeating the cycle. During the first 12 hours of the test, the one carburetor (hereinafter call the first carburetor) was operated on the untreated gasoline, while the other carburetor (hereinafter called the second carburetor) was operated on the gasoline containing the additive. At the end of this 12 hour period, the sleeves were removed, weighed, and then replaced. During the next twelve hours of operation the feed to the two carburetors was reversed so that the first carburetor now operated on the additive treated gasoline, while the second carburetor operated on the nonadditive gasoline. The sleeves were again removed and weighed. The % carburetor cleanup due to the additive was calculated as follows: the change in weight of the two sleeves during their run with the untreated gasoline were added together (first total) and from this value was subtracted the sum of the change in weight of the two sleeves during their cleanup period while operating on the additive treated gasoline (second total). The % carburetor cleanup is then calculated as follows:

$$\% \text{ cleanup} = \frac{\text{first total} - \text{second total}}{\text{first total}} \times 100$$

In this case, the carburetor cleanup was 55% indicating that the additive was very effective as a carburetor detergent when added to gasoline.

Part C — A SIB Test was carried out on the product of Part A, above, to determine its effectiveness as a sludge dispersant in lubricating oil. A set of two blanks, i.e., the SIB oil without additive, was run first. The blanks gave 17.1 and 2.7 mg. sludge per 10 grams of oil respectively. A second set of blanks gave 16.3 and 16.6 mg. sludge per 10 grams of oil, thus clearly indicating that the aforesaid 2.7 reading was in error, and could be disregarded. Blends in the SIB Test oil of 0.25 wt. % 0.50 wt. % and 0.75 wt. % of the concentrate (50% oxazoline) of Part A, gave sludge readings of 9.6, 0.3, and 0.1 mg. sludge/10 gm. of oil, respectively. Since the oil without additive gave readings of 16–17, the treated oil showed that the oxazoline concentrate was effective as a dispersant and extremely effective at the 0.50 and 0.75 wt. % concentrations.

The SIB Tests were repeated again at a later time. Here a set of 4 blanks, i.e., untreated oil, gave readings of 16.4, 17.2, 18.1 and 17.8 mg. sludge/10 gm. of oil, respectively. Two tests of the SIB oil containing 0.25 wt. % of the concentrate of Part A gave readings of 12.2 and 12.0. Two tests of the SIB oil containing 0.50 wt. % of said concentrate gave readings of 3.1 and 6.1. Tests at 0.75 wt. % and 1.0 wt. % concentrate levels each gave a reading of 0.1. 1.5 wt. % concentrate gave a reading of 0.7, and 2.0 wt. % concentrate gave a reading of 0.6. All of said preceding readings are in terms of mg. sludge per 10 grams of the test oil. This test data confirms the preceding SIB test data on the bis-oxazoline product of Part A above showing that it is an extremely effective sludge dispersant, particularly at above the 0.75 wt. % concentration level, i.e., about 0.375 wt. % active ingredient.

EXAMPLE 25

32 gm. (0.03 moles) of polyisobutenylsuccinic anhydride having a molecular weight of about 1067 was reacted with 7.2 gms. (0.06 moles) of 2-amino-2-(hydroxymethyl)-1,3-propanediol by comoining the reactants together in 100 ml. 3-neck stirred flask along with 25 ml. xylene. The temperature was raised to 200° F. for 1 hour, then the heat was turned off and the mixture was allowed to stir over a weekend. Following this the mixture was again heated to 200° F. with 3 hours of stirring. The temperature was then raised to 375° F. and the contents were blown with nitrogen to remove the xylene. After completion of the xylene removal, the mixture was then vacuum stripped at 2 mm. Hg. pressure at 375° F. for 3 hours to remove water that had formed. The reaction mixture was allowed to cool overnight while the vacuum was maintained. The following day the product was removed from the flask. The product analyzed 2.22 wt. % nitrogen as against a calculated value of about 2.20 wt. % nitrogen for the bis-oxazoline.

The product of Example 25 was tested for its effectiveness as a gasoline anti-rust agent. Since this oxazoline product was not directly soluble in gasoline, it was first dissolved in xylene, and sufficient xylene solution was then added to the gasoline to incorporate the additive at a treat rate of 10 pounds of oxazoline additive per thousand barrels of gasoline, i.e., about 0.024 wt. %. The gasoline so treated was then tested for rust according to ASTM D-665M rust test. In brief, this test is carried out by observing the amount of rust that forms on a steel spindle after rotating for an hour in a water-gasoline mixture. In this case, the oxazoline treated gasoline gave no rust indicating that it was very effective as an anti-rust additive since the untreated gasoline will give rust over the entire surface of the spindle.

Several mono-oxazoline dispersants were prepared as follows:

EXAMPLE 26

Approximately 0.2 mole of polyisobutenylsuccinic anhydride (Sap. No. 80) was charged into a reactor and heated to 205° C. under a nitrogen blanket. To the stirred reactant were added 0.2 mole (24.2 g.) of tris-(hydroxymethyl) aminomethane, in portions, over an hour period. Thereafter, the mixture was stirred at 205° C. for about 3 hours while water distilled from the reactor. Upon cooling, half of the reaction mixture was dissolved in an equal weight percent of Solvent 150 Neutral oil. The resulting oil solution was then diluted with 500 ml. of hexane and the resulting hexane solution was washed three times, each with a 250 ml. portion of methanol. Rotoevaporation of the hexane layer afforded a concentrate which analyzed for 0.50 wt. % nitrogen and 2.37 wt. % oxygen, and featured a TAN (total acid number) of 0.16. The experimentally found O/N ratio of 4.7 was in excellent agreement with the theoretical O/N ratio of 4.6. Furthermore, a strong absorption band at 6.0 microns in infrared spectrum of the product indicated a mono-oxazoline structure formed. Another strong absorption band at 5.75 micron indicated an ester structure had also formed, which is believed to be between one of the hydroxy groups extending from the oxazoline ring with a carboxy group of the polyisobutenylsuccinic anhydride.

EXAMPLE 27

1335 grams of polyisobutenylsuccinic anhydride having a Sap. No. of about 80 was charged into a 1 liter 4-necked flask, and heated to 205° C. The reactant was stirred under a nitrogen sparge and blanket and 121 grams of tris-(hydroxymethyl) aminomethane was added over a 1 hour period, being careful to avoid foaming. The course of reaction was monitored by infrared spectroscopy, which indicated that the reaction was essentially complete after eight hours. The neat product analyzed for 1.12 wt. % nitrogen and featured a number average molecular weight of 3034 (by vapor pressure osmometry). The infrared spectrum of the product showed the expected ester and oxazoline bands at 5.75 and 6.02 microns, respectively.

EXAMPLE 28

53.4 pounds of polyisobutenylsuccinic anhydride (PIBSA) with a Sap. No. of about 80 was charged into a reactor and heated to 435° F. Th PIBSA reactant was stirred and sparged with nitrogen, and 4.84 pounds of tris-(hydroxymethyl) aminomethane were added over an hour period. Reaction was continued until water evolution had ceased. The product was diluted with an equal weight of Solvent 150 Neutral oil and showed ester and oxazoline absorptions in the infrared. The oil solution analyzed for 0.51 wt. % nitrogen. Also there should be 50 to 1400 preferably about 60 to 300 carbon atoms per moiety of discarboxylic acid material. Thus, in the case of very high molecular weight polymers, they will be generally chlorinated to permit adding on a number of dicarboxylic acid groups along the chain. For example, using a polymer with 10,000 carbon atoms, one could chlorinate and the react with maleic anhydride so as to distribute about 50 maleic anhydride units randomly along the polymer chain, and then convert these maleic anhydride units into mono or bis-oxazoline units, or mixtures of mono and bis-oxazoline units.

In summary, effective additives for oleaginous compositions can be prepared by reaction of a hydrocarbon substituted dicarboxylic acid material with a 2,2-disubstituted-2-amino-1-alkanol under conditions such that formation of simple esters, imides or amides is eliminated, or at least minimized, so that a substantial proportion of the amino-alkanol is converted into oxazoline rings. Infrared spectrum on some of the aforesaid Examples indicate that a major proportion, and in some cases essentially all, of the amino-alkanol was converted to oxazoline rings.

What is claimed is:

1. A lubricating oil composition comprising: a major amount of lubricating oil and 0.01 to 20 wt. % of bis-oxazoline of a molar proportion of a hydrocarbon-substituted $C_4$-$C_{10}$ dicarboxylic acid material selected from the group consisting of dicarboxylic acid, ester and anhydrides thereof, having more than 50 carbon atoms in said hydrocarbon substituent; reacted with about two molar proportions of a 2,2-disubstituted-2-amino-1-alkanol having 2 to 3 hydroxy groups and containing a total of 4 to 8 carbons of the formula:

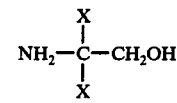

wherein X is alkyl or hydroxy alkyl, said alkyl groups having 1 to 3 carbon atoms, and at least one of said X is a hydroxy alkyl group of the structure —$(CH_2)_n$OH where $n$ is 1 to 3; at a temperature in the range of about 140° to 240° C for about ½ to 24 hours with the removal of about three molar proportions of water.

2. A composition according to claim 1, wherein said hydrocarbon-substituted dicarboxylic acid material is alkenyl succinic anhydride.

3. A composition according to claim 2, wherein said amino-1-alkanol is 2-amino-2-methyl-1-propanol.

4. A composition according to claim 2, wherein said amino-1-alkanol is tris-(hydroxymethyl)aminomethane.

5. An additive concentrate comprising: a major amount of mineral lubricating oil in the range of 98 to 45 parts by weight, 2 to 45 parts by weight of bis-oxazoline of a molar proportion of a hydrocarbon-substituted $C_4$-$C_{10}$ dicarboxylic acid material selected from the group consisting of dicarboxylic acid, ester and anhydrides thereof, having more than 50 carbon atoms in said hydrocarbon substituent; reacted with about two molar proportions of a 2,2-disubstituted-2-amino-1-alkanol having 2 to 3 hydroxy groups and containing a total of 4 to 8 carbons of the formula:

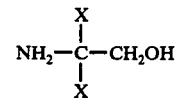

wherein X is alkyl or hydroxy alkyl, said alkyl groups having 1 to 3 carbon atoms, and at least one of said X is a hydroxy alkyl group of the structure —$(CH_2)_n$OH where $n$ is 1 to 3; at a temperature in the range of about 140° to 240° C for about ½ to 24 hours with the removal of about three molar proportions of water.

6. A concentrate according to claim 5, wherein said hydrocarbon substituted dicarboxylic acid is alkenyl succinic anhydride.

7. A concentrate according to claim 6, wherein said amino alcohol is 2-amino-2-methyl-1-propanol.

8. A composition according to claim 6, wherein said amino alcohol is tris-(hydroxymethyl)aminomethane.

9. An oil-soluble, oxazoline reaction product obtained from heating together a molar equivalent of a hydrocarbon substituted $C_4$-$C_{10}$ dicarboxylic acid material having more than 50 carbon atoms per dicarboxylic acid group, and two molar equivalents of a 2,2-disubstituted-2-amino-1-alkanol having the formula

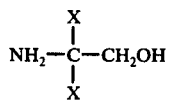

wherein X is alkyl or hydroxy alkyl, said alkyl groups having 1 to 3 carbon atoms, and at least one of said X is a hydroxy alkyl group of the structure $-(CH_2)_nOH$ where $n$ is 1 to 3 at a temperature of from 140°-240° C. until cessation of water evolution indicating completion of the oxazoline reaction.

10. An oil-soluble reaction product according to claim 9 wherein said acid material is selected from the group consisting of acids, anhydrides and esters and both of said Xs of said amino-1-alkanol formula are hydroxy alkyl groups of the structure $-(CH_2)_nOH$ wherein $n$ is 1 to 3.

11. An oil soluble reaction product according to claim 9, wherein said hydrocarbon substituted dicarboxylic acid material is an alkenyl succinic anhydride and said amino-alkanol is tris-(hydroxymethyl) aminomethane.

12. A reaction product according to claim 11, wherein said alkenyl group comprises principally a polymer of $C_2$-$C_5$ monoolefin.

13. A process for preparing the reaction product of claim 9, by heating to about 180° to 220° C a mixture of dicarboxylic acid material and said amino-alkanol, and removing a stoichiometric amount of water by continuing said heating for from about 2 to 8 hours.

14. A bisoxazoline reaction product prepared by the reaction of a molar proportion of a hydrocarbon substituted $C_4$-$C_{10}$ dicarboxylic acid material having more than 50 carbon atoms per dicarboxylic acid group and two molar proportions of a 2,2-disubstituted-2-amino-1-alkanol having the formula

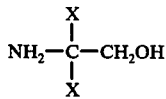

wherein X is alkyl or hydroxy alkyl, said alkyl groups having 1 to 3 carbon atoms, and at least one of said X is a hydroxy alkyl group of the structure $-(CH_2)_nOH$ where $n$ is 1 to 3 at a temperature of from 140°-240° C. until cessation of water evolution indicating completion of the oxazoline reaction.

15. A bis-oxazoline reaction product according to claim 14 wherein said reaction is carried out at a temperature of from 140°-240° C and for a time period determined by the evolution of about three molar proportions of water.

16. A composition according to claim 9, wherein said time is about 2 to 8 hours.

17. A composition according to claim 14, wherein said temperature is about 180° to 220° C. and said time is about 2 to 8 hours.

18. A bis-oxazoline of the general formula

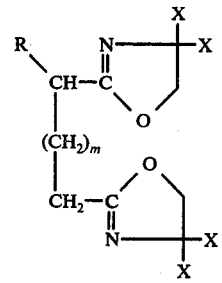

where X is an alkyl or hydroxy alkyl group said alkyl groups having 1 to 3 carbon atoms with at least one of the X substituents on each ring being a hydroxy alkyl group of the structure $-(CH_2)_nOH$ wherein $n$ is 1 to 3 and R is a substantially saturated hydrocarbyl group containing at least 50 carbon atoms and $m$ is from 0 to 6.

19. A bis-oxazoline according to claim 18 in which all of the X substituents are hydroxy alkyl groups of the structure $-(CH_2)_nOH$ wherein $n$ is 1 to 3.

20. A bis-oxazoline according to claim 18 in which $n$ is 1.

21. A bis-oxazoline according to claim 18 in which R is an olefin polymer.

22. A bis-oxazoline according to claim 21 in which the olefin is isobutylene.

23. A bis-oxazoline according to claim 21 in which the olefin polymer is of molecular weight from 10,000 to 200,000.

24. A process of preparing a bis-oxazoline comprising reacting a molar proportion of a substantially saturated hydrocarbyl-substituted $C_4$-$C_{10}$ dicarboxylic acid or anhydride or ester thereof having at least 50 carbon atoms in said hydrocarbyl group with 2 molar proportions of a 2,2-disubstituted-2-amino-1-alkanol having 2 to 3 hydroxy groups and containing a total of 4 to 8 carbons of the formula

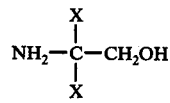

wherein X is alkyl or hydroxyalkyl, said alkyl groups having 1 to 3 carbon atoms, and at least one of said X is a hydroxy alkyl group of the structure $-(CH_2)_nOH$ where $n$ is 1 to 3, at a temperature in the range of 140° to 240° C. for ½ to 24 hours with the removal of three molar proportions of water.

25. The process according to claim 24 wherein said reaction is carried out at a temperature ranging from 180° to 220° C. for 2 to 8 hours.

26. The process according to claim 25 wherein said hydrocarbyl group is an alkenyl group.

27. The process according to claim 25 wherein said hydrocarbyl group is a polyisobutenyl group.

28. The process according to claim 25 wherein said anhydride is succinic anhydride.

29. The process according to claim 25 wherein said acid or anhydride or ester is obtained by the reaction of an olefin polymer of 900 to 3,000 number average molecular weight and having one terminal double bond per polymer chain with maleic anhydride.

30. The process according to claim 28 wherein said amino-1-alkanol is 2-amino-2-methyl-1,3-propane-diol.

31. The process according to claim 28 wherein said amino-1-alkanol is tris-hydroxy-methylaminomethane.

* * * * *